(12) United States Patent
Emmons, III

(10) Patent No.: US 8,133,052 B1
(45) Date of Patent: Mar. 13, 2012

(54) DENTAL MIRROR WITH MIRROR-CLEANING SUCTION

(76) Inventor: Donald L. Emmons, III, Covington, WA (US)

( * ) Notice: Subject to any disclaimer, the term of this patent is extended or adjusted under 35 U.S.C. 154(b) by 258 days.

(21) Appl. No.: 12/417,504

(22) Filed: Apr. 2, 2009

(51) Int. Cl.
*A61B 1/24* (2006.01)
(52) U.S. Cl. ........................................... 433/30
(58) Field of Classification Search ............ 433/30, 433/31, 29; 362/573
See application file for complete search history.

(56) References Cited

U.S. PATENT DOCUMENTS

| | | | | |
|---|---|---|---|---|
| 1,909,853 A | * | 5/1933 | Dalton | 359/882 |
| 3,928,916 A | * | 12/1975 | Hansson | 433/31 |
| 4,279,594 A | * | 7/1981 | Rigutto | 433/31 |
| 4,512,635 A | * | 4/1985 | Melde | 359/882 |
| 4,883,426 A | | 11/1989 | Ferrer | |
| 5,295,826 A | * | 3/1994 | Yandell et al. | 433/31 |
| 5,813,856 A | | 9/1998 | Lee | |

* cited by examiner

*Primary Examiner* — Cris L Rodriguez
*Assistant Examiner* — Matthew Seward

(57) ABSTRACT

A dental suction mirror with a plurality of suction ports on the periphery of the reflective surface spaced apart substantially about a forward half of the mirror with the ports directed across the reflective surface. The mirror also includes a plurality of lower suction holes directed out of the cavity downward from a bottom of the mirror. The reflective surface of the mirror is replaceable.

16 Claims, 5 Drawing Sheets

DENTAL MIRROR WITH MIRROR-CLEANING SUCTION

BACKGROUND

1. Field of the Invention

This invention pertains to dental implements, and more specifically to a dental mirror with suction ports on the periphery of the mirror that cleans the mirror reflective surface by drawing air across the reflective surface during a dental procedure.

2. Prior Art

It is known to have dental mirrors to facilitate various treatments by the dentist or hygienist. It is also known to have dental mirrors that include suction ports that draw fluids and debris through the mirror and out the mirror handle, allowing the dentist or hygienist to proceed without the involvement of an assistant using a separate suction hose and without a suction hose that hooks on the user's mouth. Suction ports in these mirrors previously have been directed radially outward from the mirror from a circular mirror, such as described in U.S. Pat. No. 5,813,856 by Lee, to draw from the patient's mouth but with no function of keeping the reflective surface of the mirror clean. Dental mirrors commonly become obscured by water introduced by another dental implement or by patient saliva or by debris ancillary to the dental procedure.

The reflective surface of mirrors also frequently gets scratched or otherwise damaged. Previously, the entire mirror must be discarded. It would be advantageous to be able to replace the reflective surface without replacing the entire mirror to reduce costs.

It is therefore an object of the present invention to provide a dental mirror that is maintained unobscured by fluids and debris within the patient's mouth while also providing for removal of those fluids and debris out of the mouth by suction. It is also an object that the reflecting surface of the mirror be replaceable so the entire mirror unit would not need to be discarded each time a reflective surface, thus reducing the costs of using suction mirrors.

SUMMARY

These objects are achieved first by a typically circular self-cleaning dental mirror that maintains the mirror reflective surface unobstructed during a dental procedure by drawing air across the reflective surface and second by providing for removal and replacement of just the reflective surface of the mirror. Additionally, to remove fluids and debris from a patient's mouth, suction holes are provided in the bottom of the mirror, under the reflective surface of the mirror, where they are more convenient to use than if they were directed radially outward.

The mirror includes a tubular handle that extends rearward from a mirror rearward, or proximal, half and is connectable to a suction device at one end. The handle other end opens into a mirror cavity. Suction ports between the cavity and the reflective surface are spaced apart about the forward, or distal, half of the periphery of the reflective surface and are directed over its surface thus providing fluid communication between the suction device and the reflective surface. Lower suction holes are also provided that are directed downward out of the cavity to facilitate withdrawal of saliva and water from the patient's mouth. (For these purposes, downward is deemed to mean in the cavity bottom and directed away from the reflecting surface). Both suction ports directed over the reflective surface, that is on the top or front of the mirror, and suction holes below the reflective surface, that is on the bottom or back of the mirror, connect to the mirror cavity. Therefore, blocking to close either set of holes or ports during use increases the effective suction through the other set. This may occur, for example, when the reflective surface is used to retract the tongue and cheek which blocks the suction ports at the reflective surface giving additional suction to the suction holes on the back of the mirror, which is advantageous in removing debris from the mouth.

To effectively draw liquids and debris from off the reflective surface suction from the suction device must be maximized. It has been empirically determined that ports in the rearward half of the periphery of the reflective surface are substantially ineffective in removing matter from the reflective surface and rob suction from the ports at the forward half of the periphery. It is therefore important that there be ports only at the forward half.

The reflective surface is provided on a removable plate than can be installed and removed from the mirror. The plate functions as a cover for the mirror cavity so the plate is installed by inserting it into the cavity and then rotating it into place. The plate is inserted into the cavity through a pair of suction ports located on a diameter of the mirror that divides the forward half of the mirror from the rearward half. (For these purposes of description the handle is on the proximal, or rearward half of the mirror and the forward half is away from the handle.) As the plate is inserted into the cavity it depresses a resilient forward support that urges the plate upward when the plate is released. The plate is inserted until the rearward portion of the plate clears a rearward rim that extends around the rearward half of the periphery at which point the plate slips entirely into the cavity. The forward corner of the rearward support serves as a fulcrum on which the plate rotates when in the cavity by action of the forward support pushing upward on the forward half and a user pushing downward on the rearward half against a rearward support. Typically, the fulcrum at the forward corner of the rearward support is located slightly rearward of to the diameter that divides the forward and rearward halves and may extend from sides of the cavity parallel to that diameter. It was experimentally determined that that location is required to allow room in the cavity for the plate to rotate and then slide into place.

When released by the user, the plate is urged upward by the forward support against a forward rim extending around the forward half of the periphery of the mirror when it is in its operational position. Installation of the plate is then completed by urging it rearward against the rearward cavity wall, resulting in into an effective seal around the entire periphery of the plate thus substantially preventing air flow except through suction ports. The forward rim is necessarily larger than the rearward rim because it must receive the plate in a temporary forward position as the plate is rotated and then must still support the plate when the plate is slid rearward under the rearward rim.

With the mirror installed air may be drawn through the upper suction slots from across the mirror and out the handle, cleaning the mirror of fluid and debris. Air is also drawn through the suction holes.

DETAILED DESCRIPTION OF THE PREFERRED EMBODIMENTS

Figure 1:
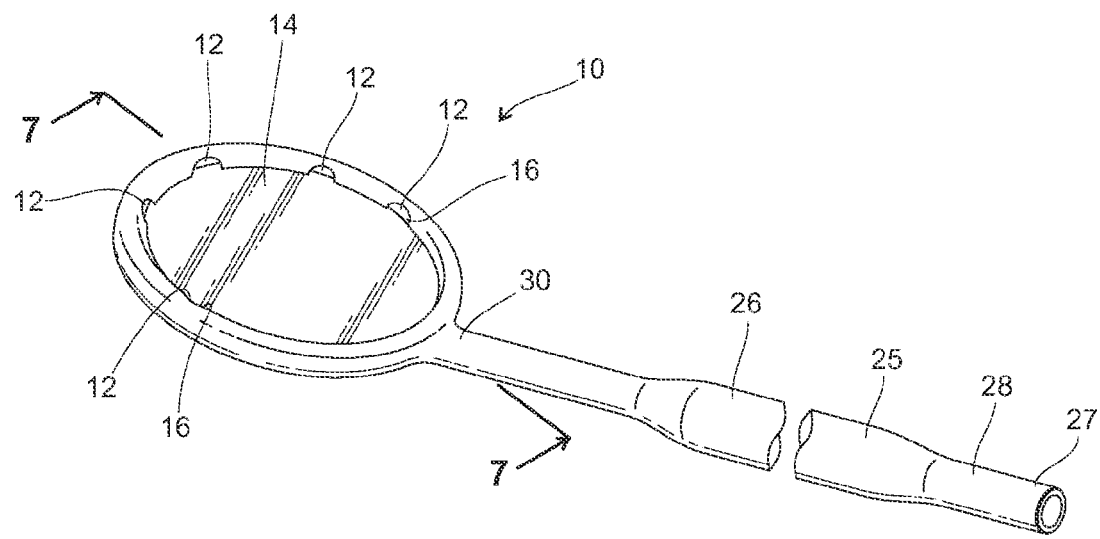
FIG. 1 is a top perspective view of the suction mirror of the present invention.
Figure 2:
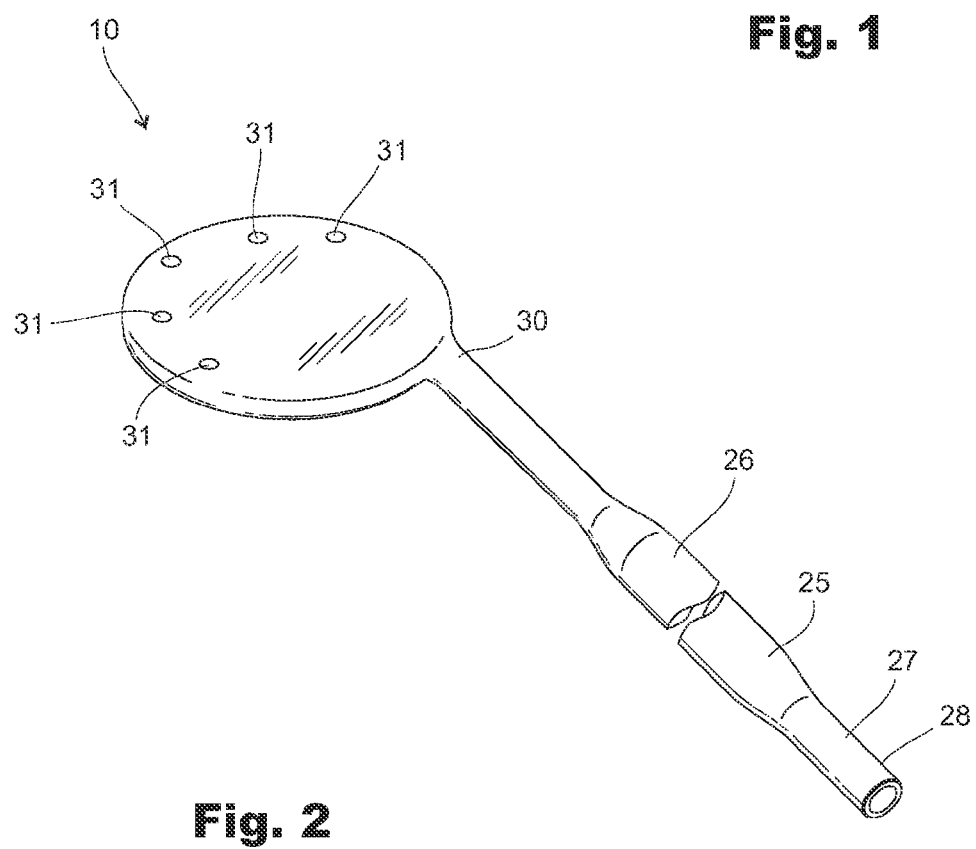
FIG. 2 is a bottom perspective view of the suction mirror of FIG. 1.
Figure 3:
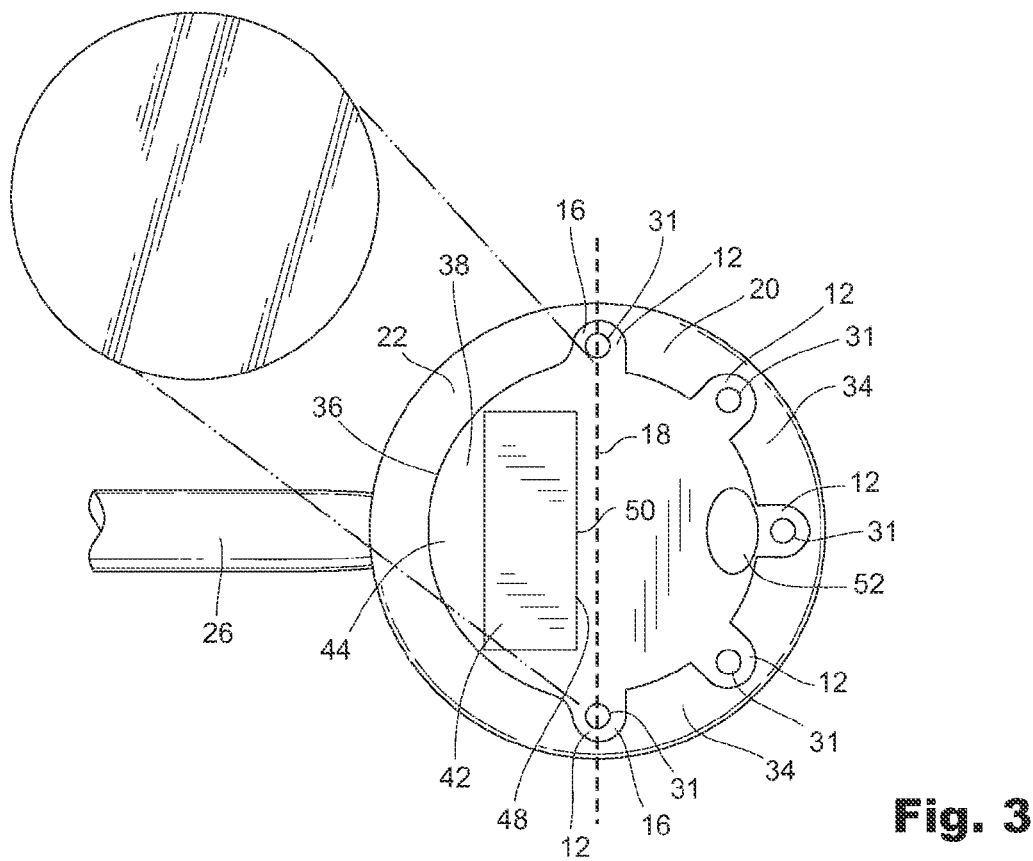
FIG. 3 is a top view of the suction mirror of FIG. 1, showing the mirror reflecting plate aligned for installation.
Figure 4:
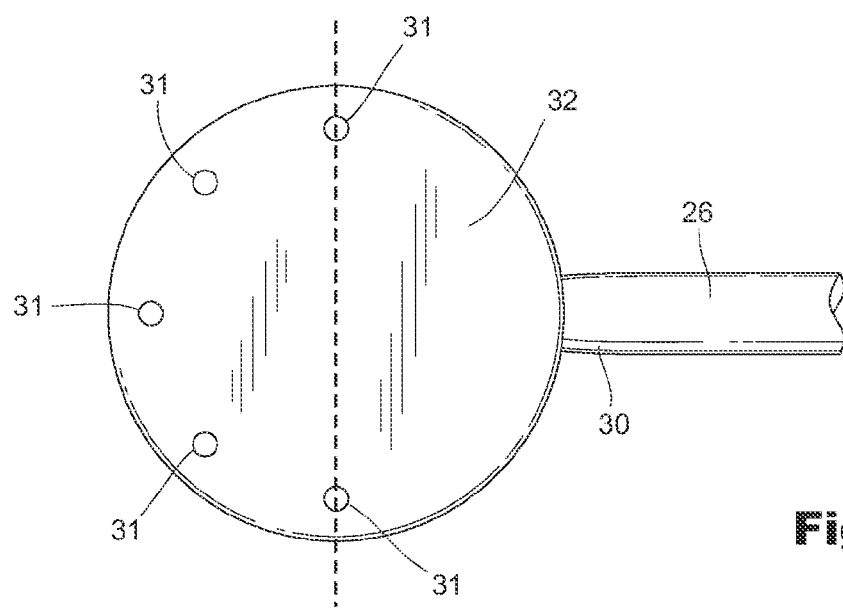
FIG. 4 is a bottom view of the suction mirror of FIG. 3.
Figure 5:
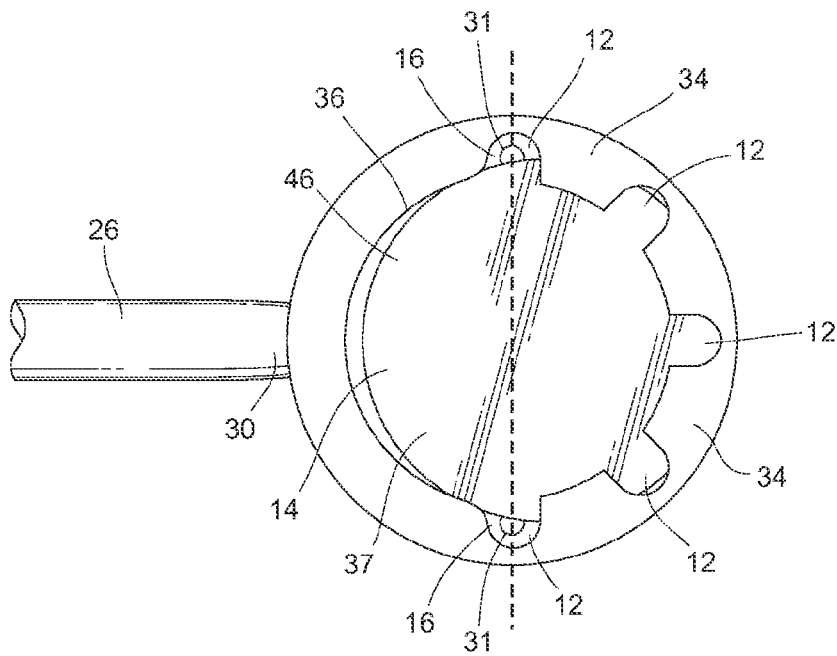
FIG. 5 is a top view of the mirror of FIG. 3 with the mirror reflecting plate inserted through diametrically opposed access ports and still forward, preparatory for sliding rearward into its installed position.
Figure 6:
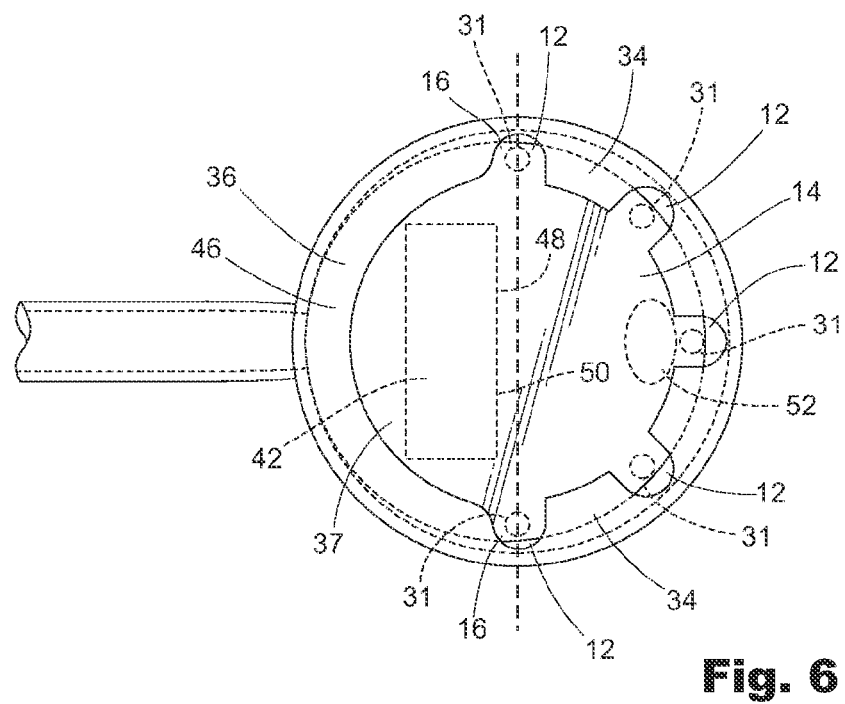
FIG. 6 is a top view of the suction mirror of FIG. 3 with the mirror reflecting plate in its installed position.
Figure 7:
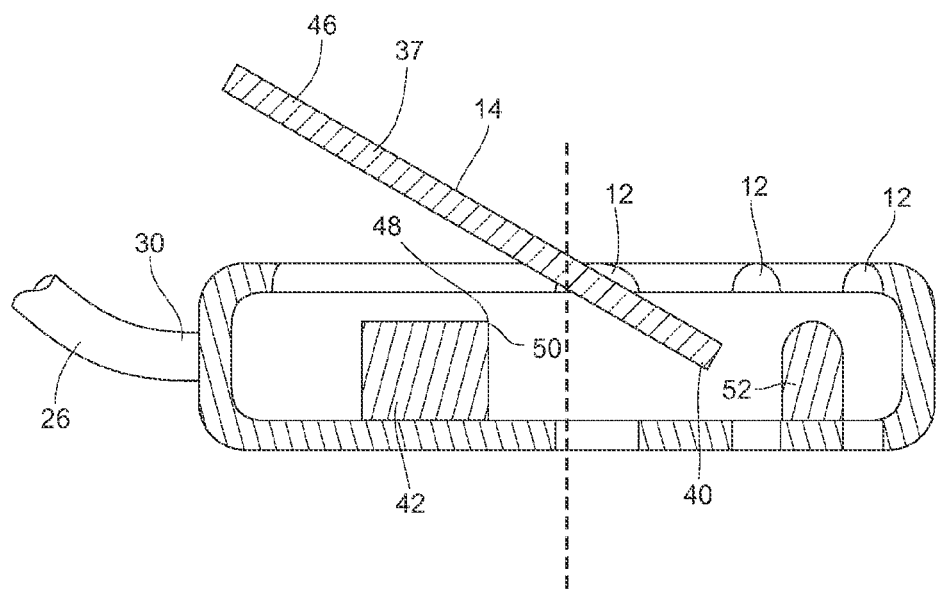
FIG. 7 is a side cross sectional view of the mirror of FIG. 1 along the line 7-7 shown in FIG. 1, showing the mirror reflecting plate slightly inserted through access ports.
Figure 8:
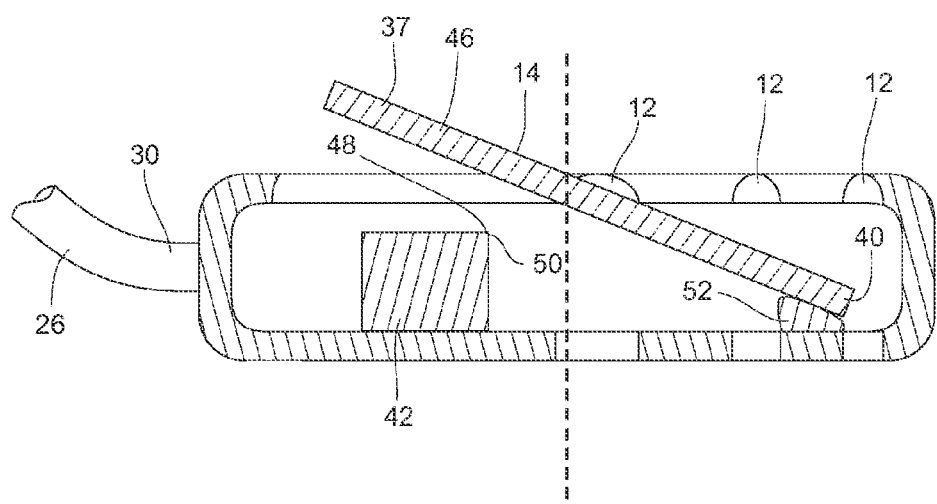
FIG. 8 is a side cross sectional view of the mirror of FIG. 7, showing the mirror reflecting plate further inserted through the access ports.
Figure 9:
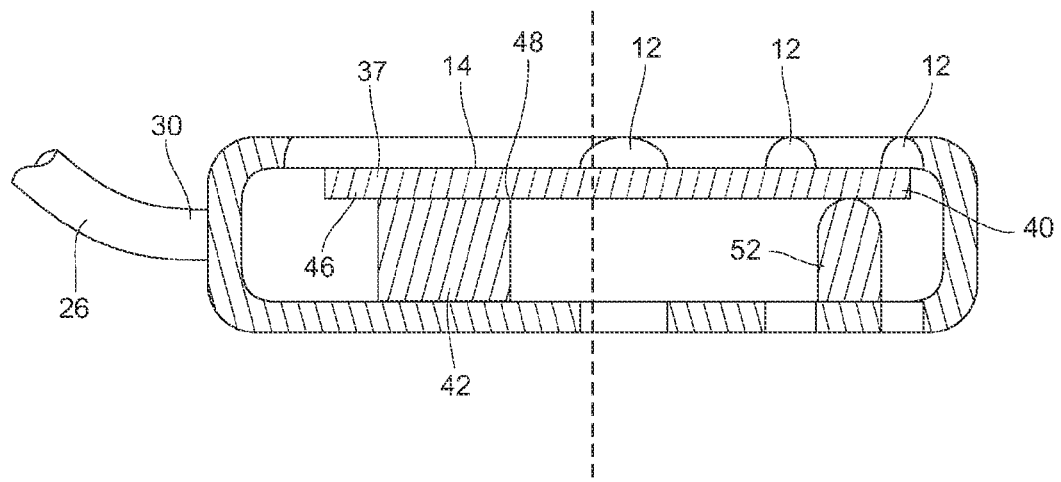
FIG. 9 is a side cross sectional view of the mirror of FIG. 8, showing the reflecting plate forward in horizontal position, having cleared the lip rearward on the mirror.
Figure 10:
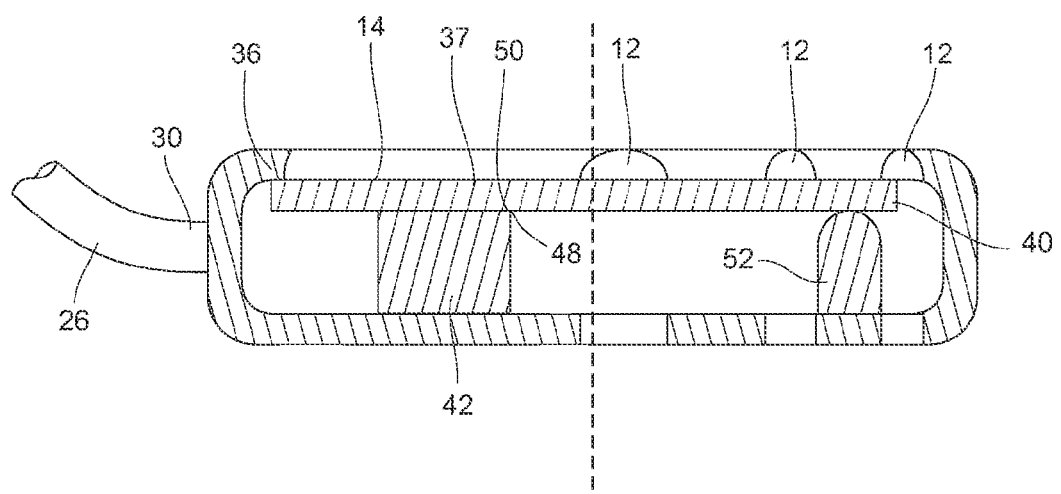
FIG. 10 is cross sectional view of the mirror of FIG. 9 showing the reflecting plate rearward in its installation position.

The dental mirror 10 of the present invention includes mirror cleaning suction through a plurality of suction ports 12 on the periphery of the mirror's reflective surface 14. The ports 12 are spaced apart about a forward half of the mirror 10 with the suction ports 12 directed across the reflective surface 14, two of which also function as a pair of access ports 16 whose centers lie on a diameter 18 dividing mirror forward and rearward halves 20, 22.

A handle 26 extends from central in the rearward half 22 of the mirror 10 and provides fluid communication through the handle 26 between a suction device (not shown) connectable to a handle first end 28. Dental offices employ low and high speed suction vacuum lines. Small vacuum lines of about 0.25-inch diameter and large vacuum lines of about 7/16-inch diameter are used with the respective low and high speed suction vacuum lines to assure implements are correctly connected to the required suction line. The handle 26 accommodates both suction lines with a larger diameter stem 25 for receiving a larger diameter vacuum line and tapering down to a smaller diameter stem 27 for receiving a smaller diameter vacuum line.

The mirror 10 includes a cavity 29 in fluid communication with a handle second end 30 with the suction ports 12 opening into the cavity 29 such that suction applied to the suction handle first end 28 draws air across the mirror reflecting surface 14 and out the suction handle first end 28. The mirror 10 further includes a plurality of lower suction holes 31 on the mirror forward half 20 directed out of the cavity 29 downward from a bottom 32 of the mirror 10. The cavity 29 is sealed about its periphery with an equatorial wall 55, which allows for fluid communication only between the handle 26; and the ports 12, and suction holes 31.

A forward rim 34 is located on the forward half 20 of the mirror 10 and a rearward rim 36 of inner radius greater than the forward rim 34 is located on the rearward half 22 of the mirror 10 separated by the access ports 16. The reflective surface 14 of the mirror is the top of a removable plate 37 that covers a top 38 of the cavity 29 and a bottom 24 of the cavity 29. During installation of the plate 37 a forward portion 40 of the plate 37 is slidable into the cavity 29 and under the forward rim 34 through the access ports 16.

A resilient forward support 52 forward in the cavity 29 is depressed by the forward portion 40 of the plate 37 as it slides into the cavity 29 through the access ports 16. Access ports 16 are shaped to allow the mirror to drop under the rearward rim 36 when the mirror is slid forward but, not allow the mirror to move past the rearward rim 36 when the mirror is slid backward and locked in place. It may be a spring or resilient rubber plug that is pressed into the back side of the suction mirror or other functionally equivalent member. A rearward support 42 is located rearward in the floor 44 of the cavity 29 to support a rearward portion 46 of the plate 37. During installation (and removal), after the plate 37 is inserted fully within the cavity 29, the plate 37 rotates on a support fulcrum 48, which is typically the forward corner 50 of the rearward support 42. As the rearward portion 46 of the plate 37 clears the rearward rim 36, the forward support 52 urges the forward portion 40 of the plate 37 upward against the forward rim 34 providing an effective seal with the rearward portion 46 of the plate 37 urged downward against the rearward support 42 as the plate 37 rotates on the fulcrum 48. The plate 37 is then urged rearward on the rearward support 42 under the rearward rim 36 until it abuts a matching surface of the cavity wall, providing an effective seal. Thus, the plate 37 is supported by the rearward and forward supports 42, 52 under the rearward and forward rims 40, 34.

The mirror plate 37 is removable by urging the plate forward until it clears the rearward rim 36 and then downward against the forward support 52 until it intercepts the access ports 16. It is then withdrawn through the access ports 16.

Having described the invention, what is claimed is as follows:

1. A dental mirror with mirror cleaning suction, comprising a mirror having a reflective surface and with a plurality of suction ports on the periphery of the reflective surface with the suction ports directed across the reflective surface, a handle extending from the mirror and providing fluid communication through the handle between a suction device connectable to a handle first end and the mirror at a handle second end, the suction ports in fluid communication with the handle second end such that suction applied to the suction handle first end draws air across the mirror reflective surface and out the suction handle first end, wherein the mirror includes a cavity in fluid communication with the handle second end, the suction ports opening into the cavity, wherein, a forward rim is on the forward half of the mirror and a rearward rim is on the rearward half of the mirror, and wherein the reflective surface comprises a removable plate that covers a top of the cavity, the plate secured under the rims when installed on the mirror, and wherein two of which suction ports function as a pair of access ports, which access ports are diametrically opposed with centers on a diameter dividing the mirror forward and rearward halves through which access ports a forward portion of the plate is slidable into the cavity and under the forward rim during installation of the plate, a rearward support rearward in the cavity, a support fulcrum in the cavity, a resilient forward support forward in the cavity depressed by the forward portion of the plate as it slides into the cavity during installation, wherein as a rearward portion of the plate clears the rearward rim, the forward support urges the forward portion of the plate upward against the forward rim with the rearward portion of the plate urged downward against the rearward support as the plate rotates on the fulcrum, such that after the plate is urged rearward on the rearward support under the rearward rim the plate is supported by the rearward and forward supports under the rearward and forward rims.

2. The dental mirror of claim 1 wherein the mirror includes a plurality of lower suction holes directed out of the cavity downward from a bottom of the mirror.

3. The dental mirror of claim 1 wherein the suction ports are spaced apart substantially about a forward half of the mirror with the handle extending from central in a rearward half of the mirror.

4. The dental mirror of claim 3 wherein the plurality of suction ports comprise a pair of ports with centers on a diameter that divides mirror forward and rearward halves.

5. The dental mirror of claim 1 wherein the suction ports are spaced apart substantially about a forward half of the mirror with the handle extending from central in a rearward half of the mirror, and wherein the plurality of ports comprise a pair of ports with centers on a diameter that divides mirror forward and rearward halves.

6. The dental mirror of claim 1 wherein the forward rim is of inner radius smaller than the rearward rim.

7. The dental mirror of claim 1 wherein the forward rim is separated from the rearward rim by said access ports.

8. The dental mirror of claim 1 wherein the mirror is removable by urging the plate forward until it clears the rearward rim and then its forward half downward against the forward support until it intercepts the access ports and then out the access ports.

9. A dental mirror with mirror cleaning suction, comprising
a mirror with a reflective surface with a plurality of suction ports on the periphery of the reflective surface with the suction ports directed across the reflective surface,
a handle extending from the mirror and providing fluid communication through the handle between a suction device connectable to a handle first end and the mirror at a handle second end, the suction ports in fluid communication with the handle second end such that suction applied to the suction handle first end draws air across the mirror reflective surface and out the suction handle first end,
wherein the suction ports are spaced apart substantially about a forward half of the mirror with the handle extending from central in a rearward half of the mirror, two of which suction ports function as a pair of access ports, which access ports are diametrically opposed with centers on a diameter dividing the mirror forward and rearward halves,
wherein a forward rim on the forward half of the mirror and a rearward rim on the rearward half of the mirror, and
wherein the reflective surface comprises a removable plate that covers a top of the cavity, the plate secured under the rims when installed on the mirror, and
wherein a forward portion of the plate is slidable into the cavity through the access ports and under the forward rim during installation of the plate,
a rearward support rearward in the cavity,
a support fulcrum in the cavity,
a resilient forward support forward in the cavity depressed by the forward portion of the plate as it slides into the cavity during installation, wherein as a rearward portion of the plate clears the rearward rim, the forward support urges the forward portion of the plate upward against the forward rim with the rearward portion of the plate urged downward against the rearward support as the plate rotates on the fulcrum, such that after the plate is urged rearward on the rearward support under the rearward rim the plate is supported by the rearward and forward supports under the forward and rearward rims.

10. The dental mirror of claim 9 wherein the mirror includes a cavity in fluid communication with the handle second end, the suction ports opening into the cavity.

11. The dental mirror of claim 10 wherein the mirror includes a cavity in fluid communication with the handle second end, the suction ports opening into the cavity.

12. The dental mirror of claim 11 wherein the suction ports are spaced apart substantially about a forward half of the mirror with the handle extending from central in a rearward half of the mirror, two of which suction ports function as a pair of access ports, which access ports are diametrically opposed with centers on a diameter dividing the mirror forward and rearward halves.

13. The dental mirror of claim 12 wherein the mirror includes a plurality of lower suction holes directed out of the cavity downward from a bottom of the mirror.

14. A dental mirror with mirror cleaning suction, comprising
a mirror with a reflective surface with a plurality of suction ports on the periphery of the reflective surface spaced apart substantially about a forward half of the mirror with the suction ports directed across the reflective surface,
two of which suction ports function as a pair of access ports, which access ports are diametrically opposed with centers on a diameter dividing the mirror forward and rearward halves,
the mirror including a cavity in fluid communication with a handle second end, the suction ports opening into the cavity, the mirror further including a plurality of lower suction holes directed out of the cavity downward from a bottom of the mirror,
a handle extending from central in a rearward half of the mirror and providing fluid communication through the handle between a suction device connectable to a handle first end and the cavity at a handle second end, such that suction applied to the suction handle first end draws air across the mirror and out the suction handle first end,
and further comprising a forward rim on the forward half of the mirror and a rearward rim on the rearward half of the mirror, and
wherein the reflective surface comprises a removable plate that covers a top of the cavity, a forward portion of the plate being slidable into the cavity and under the forward rim through the access ports during installation of the plate, the plate being secured under the rims,
a rearward support rearward in the cavity,
a support fulcrum in the cavity,
a resilient forward support forward in the cavity depressed by the forward portion of the plate as it slides into the cavity during installation, wherein as a rearward portion of the plate clears the rearward rim, the forward support urges the forward portion of the plate upward against the forward rim with the rearward portion of the plate urged downward against the rearward support as the plate rotates on the fulcrum, such that after the plate urged rearward on the rearward support under the rearward rim the plate is supported by the rearward and forward supports under the forward and rearward rims,
wherein the forward rim is of inner radius smaller than the rearward rim, and
wherein the forward rim is separated from the rearward rim by said access ports.

15. The dental mirror of claim 1 wherein the mirror is removable by urging the plate forward until it clears the rearward rim and then downward against the forward support until it intercepts the access ports and then out the access ports.

16. The dental mirror of claim 1 wherein the handle further comprises a larger diameter stem adapted to receive a larger diameter vacuum line tapering to a smaller diameter stem adapted to receive a smaller diameter vacuum line.

* * * * *